(12) United States Patent
Shiuan

(10) Patent No.: US 7,033,814 B2
(45) Date of Patent: Apr. 25, 2006

(54) METHODS FOR PREPARING YEAST WITH IMPROVED BIOTIN PRODUCTIVITY USING INTEGRATING PLASMIDS ENCODING BIOTIN SYNTHASE

(75) Inventor: David Shiuan, Kaohsiung (TW)

(73) Assignee: National Science Council, Taipei (TW)

( * ) Notice: Subject to any disclaimer, the term of this patent is extended or adjusted under 35 U.S.C. 154(b) by 489 days.

(21) Appl. No.: 09/752,957

(22) Filed: Jan. 2, 2001

(65) Prior Publication Data

US 2003/0104584 A1 Jun. 5, 2003

(30) Foreign Application Priority Data

Oct. 7, 2000 (TW) .............................. 89120972 A

(51) Int. Cl.
*C12N 1/20* (2006.01)
(52) U.S. Cl. .............................. 435/252.2; 435/252.22; 435/252.2; 435/477; 435/483
(58) Field of Classification Search ................ 435/477, 435/254.2, 483, 254.22
See application file for complete search history.

(56) References Cited

FOREIGN PATENT DOCUMENTS

GB 2216530 A * 10/1989

OTHER PUBLICATIONS

Steams et al. Manipulating yeast genome using plasmid vectors. Methods in Enzymology (1990) 185: 280-297.*
Zhang et al. The gene for biotin synthase from *Saccharomyces cerevisiae*: cloning, sequencing, and complementation of *Escherichia coli* strains lacking biotin synthase. Arch Biochem Biophys (1994) 309(1): 29-35.*
Hong et al. Candida utilis biotin synthase (Bio2) gene, complete cds. GenBank Accession No. AF212161, publicly available Dec. 7, 2000.*
Rodriguez et al. Development of an integrative DNA transformation system for the yeast Candida utilis. FEMS Microbiol Lett (1998) 165(2): 335-340.*
K.Kondo, et al.; A Transformation System for the Yeast *Candida utilis:* Use of a Modified Endogenous Ribosomal Protein Gene as a Drug-resistant Marker and Ribosomal DNA as an Integration Target for Vector DNA; Journal of Bacteriology, Dec. 1995; pp. 7171-7177.
P.Dehoux, et al.; Natural Cycloheximide Resistance in Yeast The Role of Ribosomal Protein L41; Eur.J.Biochem. 213, 1993 pp. 841-848.
S. Kawai, et al.; Drastic Alteration of Cycloheximide Sensitivity by Substitution of One Amino Acid in the L41 Ribosomal Protein of Yeasts; Journal of Bacteriology, Jan. 1992; pp. 254-262.

* cited by examiner

*Primary Examiner*—Kathleen M. Kerr
*Assistant Examiner*—Hope Robinson
(74) *Attorney, Agent, or Firm*—Thomas, Kayden, Horstemeyer & Risley

(57) ABSTRACT

Methods for preparing yeast with improved biotin productivity using integrating plasmids encoding biotin synthase. The yeast is transformed by an integrating plasmid, which includes a *Candida utilis* biotin synthase gene BIO2, an assistant DNA sequence to promote integration of the plasmid into the *C. utilis* genome, a promoter sequence, and a selection marker. Other embodiments include *Saccharomyces cerevisiae* integrating plasmids.

5 Claims, 13 Drawing Sheets

SEQUENCE LISTING

<160> NUMBER OF SEQ ID NOS: 5

<210> SEQ ID NO 1
<211> LENGTH: 1188
<212> TYPE: DNA
<213> ORGANISM: Candida utilis

<400> SEQUENCE: 1

```
atgtcgttta tattgactgc tattagtcgt ccgattgctc tttccacttc tagagtagct     60
tctagggcta ctctggcaac aggtgctact gctgctgcgg agatcttgga agatgtgttc    120
acggaacaaa tggaagaagt ggcttcacag gagaagaagc caaacccatt ggaatatgca    180
ttgtcagtga agacaccagt caacacctgg accaaagaag aaattaaagc tatatatgac    240
acaccactca tggacttgat gcactatgct caggtgcaac acagaaggtt ccaacaacct    300
tcagaggttc aattgtgcac tcttatgaat atcaaaactg gtggttgtac cgaggactgt    360
aagtactgtg cccaatcaca gcgttacaac actggtgtca aggctgaaag aatcatccaa    420
gttgatgagg tgattgaagc tgcaaaggag gcaaaggcca atggatctac aaggttctgt    480
atgggtgctg cttggagaga gatgaaaggt agaaagtcaa acttgaagaa aatcaaagag    540
atgatcactg ctgtccatga ccttggaatg gagagttgtg tcaccctggg aatggttgat    600
aaagaccaag ccactgaatt gaaaagtgct gggttgacgg cgtacaacca taacattgat    660
acttacaagg aacactatcc aaaggtgatc tccacaagaa gctttgatga tagattgaaa    720
```

```
acattcaaaa acgttcaagg atctggatta aaggcatgca caggtggtat tcttggtctt    780
ggtgagaccc aagaggaccg tgtatctttc ctctacacct tggccacaat ggatcagcat    840
ccagagtctc ttccaatcaa cagactggtc ccaatcaagg gcacgccaat gtatgaagaa    900
gttaagaaca agcaagttga agttgatgag attgtcagaa ccattgctac tgcaagattg    960
gtcatgccaa cgtctattat cagattggct gcaggaagat atacaatgaa agaggcagaa    1020
caggtgatgt gcttcatggc tggttgtaat gccatcttca caggtaagaa aatgctcaca    1080
acaatgtgta acggctggga tgaggataaa gccatgttgg ctaaatgggg tctgaaacca    1140
atggagagtt tcaaatacaa accaagggag gttgcattcg gtgcttga                1188
```

```
<210> SEQ ID NO 2
<211> LENGTH: 30
<212> TYPE: DNA
<213> ORGANISM: artificial sequence
<220> FEATURE:
<223> OTHER INFORMATION: primer sequence

<400> SEQUENCE: 2
gaaagtcgac tcaagatctg tcgtacttaa                                     30

<210> SEQ ID NO 3
<211> LENGTH: 21
<212> TYPE: DNA
<213> ORGANISM: artificial sequence
<220> FEATURE:
<223> OTHER INFORMATION: primer sequence

<400> SEQUENCE: 3
ccgcagttaa atcgacaact g                                              21

<210> SEQ ID NO 4
<211> LENGTH: 23
<212> TYPE: DNA
<213> ORGANISM: artificial sequence
<220> FEATURE:
<223> OTHER INFORMATION: primer sequence
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: R is A or G'
<220> FEATURE:
<221> NAME/KEY: misc_feature
<222> LOCATION: (12)..(12)
<223> OTHER INFORMATION: Y is T or C
<220> FEATURE:
<221> NAME/KEY: misc_feature
<222> LOCATION: (15)..(15)
<223> OTHER INFORMATION: Y is T or C
<220> FEATURE:
<221> NAME/KEY: misc_feature
<222> LOCATION: (18)..(18)
<223> OTHER INFORMATION: n is a, c, g, or t

<400> SEQUENCE: 4
tgtncngarg aytgyaanta ttg                                            23

<210> SEQ ID NO 5
```

```
<211> LENGTH: 20
<212> TYPE: DNA
<213> ORGANISM: artificial sequence
<220> FEATURE:
<223> OTHER INFORMATION: primer sequence
<220> FEATURE:
<221> NAME/KEY: misc_feature
<222> LOCATION: (3)..(3)
<223> OTHER INFORMATION: R is A or G'
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (9)..(9)
<223> OTHER INFORMATION: R is A or G'
<220> FEATURE:
<221> NAME/KEY: misc_feature
<222> LOCATION: (12)..(12)
<223> OTHER INFORMATION: R is A or G'

<400> SEQUENCE: 5
gtrtcnanrt trtggttgta                                            20
```

METHODS FOR PREPARING YEAST WITH IMPROVED BIOTIN PRODUCTIVITY USING INTEGRATING PLASMIDS ENCODING BIOTIN SYNTHASE

"This Application claims benefit under 35 USC 119 (a–d) to EPO 03100005.2 filed on Jan. 7, 2003".

BACKGROUND OF THE INVENTION

1. Field of the Invention

The present invention relates to a method for the expression of biotin using edible yeast as a host, and more particularly, to a method for highly expressing biotin using edible yeast transformed by a genetically engineered plasmid.

2. Description of the Related Arts

Biotin (2'-keto-3,4-imidazolido-2-tetrahydrothiophene-n-valeric acid) was isolated from egg yolk by Kogl and Tonuis in 1936 and named as vitamin H. It is one of the essential vitamins for nutrition of animals, plants, and microorganisms, and very important as medicine or as a food additive. In general, biotin serves as a $CO_2$ carrier for covalent binding in cells, and plays the role of coenzyme for carboxylase, decarboxylase, and transcarboxylase.

Biotin biosynthesis of *Escherichia coli* has been studied well, and the related genes are clarified. The structures and regulations of the bio operon in *E. coli* also have been thoroughly identified (Shiuan, D., et al., *Gene* 145:1–7, (1994)). This operator is located at the 17 min on the *E. coli* genomic map, which includes 5 key-enzyme genes for the biotin biosynthesis (referring to FIG. 1). The transcription of the 5 genes of the bioABFCD operon is controlled by a regulatory region located between bioA and bioB. This regulatory region consists of a 40-bp long operator sequence, partially overlapping the promoter. In addition, bioA gene and bioBFCD genes are transcribed bi-directionally from the regulatory region.

Another birA gene whose product is the repressor of the operator is located at the 89 min on the *E. coli* genomic map. The repression of transcription of the operator requires the actions of the repressor and co-repressor (i.e. biotinyl-5'-adenylate) together with the operator. Further, the biotinyl-5'-adenylate is produced by the activation of biotin by the gene product of the birA (one function of which is bio repressor, and another is biotin holo enzyme synthetase).

With respect to yeast, it is known that there are 3 biosynthesis genes in wine-making yeast, *Saccharomyces cerevisae*: BIO2 (encoding for biotin synthase), BIO3 (encoding for 7,8-diaminopelargonic acid aminotransferase), and BIO4 (encoding for dethiobiotin synthase), which correspond to bioB, bioA, and bioD genes in *E. coli*, respectively. That is, the last three steps of biotin biosynthesis in *S. cerevisae* are the same as those in *E. coli*; however, the first two steps may be different so that *S. cerevisae* cannot produce biotin from simple carbon sources. In addition, it was found recently that *S. cerevisae* possesses a BIO5 gene, which the gene product thereof is associated with the uptake of biotin and thus named as biotin permease (Phalip, V., et al., *Gene* 232:43–51 (1999)). With respect to edible yeast, *Candida utilis*, the biosynthesis of biotin remains unclear, and no related gene or enzyme has been identified. It is only understood that *S. cerevisae* should be cultured in the presence of biotin while *C. utilis* is not present, indicating that *C. utilis* is able to synthesize biotin from simple carbon sources.

Most organisms require biotin to survive, and only a few organisms can synthesize biotin themselves. The conditions due to lack of biotin in human and animals are not common; however, under some hereditary diseases or dystrophy, the lack of biotin usually results in severe consequence. For example, babies that lack holocarboxylase synthase usually have symptoms such as vomiting or asthma from the first day they are born; babies that lack biotindase may have disorders with skin, eye, and urinary system when 2–3 years old. In the past 10 years, it has been found that biotin is associated with the problems of farm animals that are bred on a large-scale. It is notable in poultry, for example, having fatty liver and kidney syndrome (FLKS), and acute death syndrome (ADS) in chicken. In 1977, it is also found that the cyllopodia (crooked-foot disease) in indoor-bred pigs is associated with the lack of biotin. Therefore, the demand of biotin increases 15% per year, in which 60–80% of biotin is used as feed additives.

In conventional methods, the production of biotin is carried out by chemical-synthetic processes, in which a crystalline biotin with high purity can be obtained for the use of medication. However, the separation and purification of the product requires very complicated steps. Moreover, in the prior art, methods for producing compounds by genetic engineering mostly employ the conventional replicative plasmid. It usually requires antibiotics to stabilize the copy number of the replicative plasmid, and thus, it is not appropriate for long-term fermentation and for food and feed. Therefore, there is still a need for development of yeast with high biotin-productivity for the use of feed additives, food additives, or cosmetics. Because the edible yeast itself is traditional food and feed, the yeast with high biotin-productivity prepared by the present invention can be formulated directly to merchandise after the processes of fermentation, separation, and drying without complicated purification. Further, the present invention uses integrated plasmid in lieu of replicative plasmid for the transformation of such genes into yeast genome, so that a stable yeast strain for high production of biotin is obtained.

SUMMARY OF THE INVENTION

In one aspect, the present invention features an integrated plasmid, which comprises a biotin synthase gene; an assistant DNA sequence for the integration of the plasmid into a host genome; a promoter sequence; and a selection marker. The construct of the plasmid can insert the biotin biosynthesis genes into a yeast genome to prepare yeast for high biotin-productivity.

In another aspect, the present invention features a method for preparing a yeast with high biotin-productivity, which comprises constructing an integrated plasmid comprising a biotin synthase gene, an assistant DNA sequence for the integration of said plasmid into a host genome, a promoter sequence, and a selection marker; linearizing said integrated plasmid; transforming said linearized integrated plasmid into a yeast; and recombining the biotin synthase gene with the yeast genome.

In still another aspect, the present invention features a method for producing biotin, which comprises providing the yeast with high biotin-productivity set forth above; and culturing said yeast in a nutrient medium, and recovering biotin from the culture broth.

BRIEF DESCRIPTION OF THE DRAWINGS

The present invention will be more fully understood and further advantages will become apparent when reference is made to the following description of the invention and the accompanying drawings in which.

DETAILED DESCRIPTION OF THE INVENTION

Figure 1:
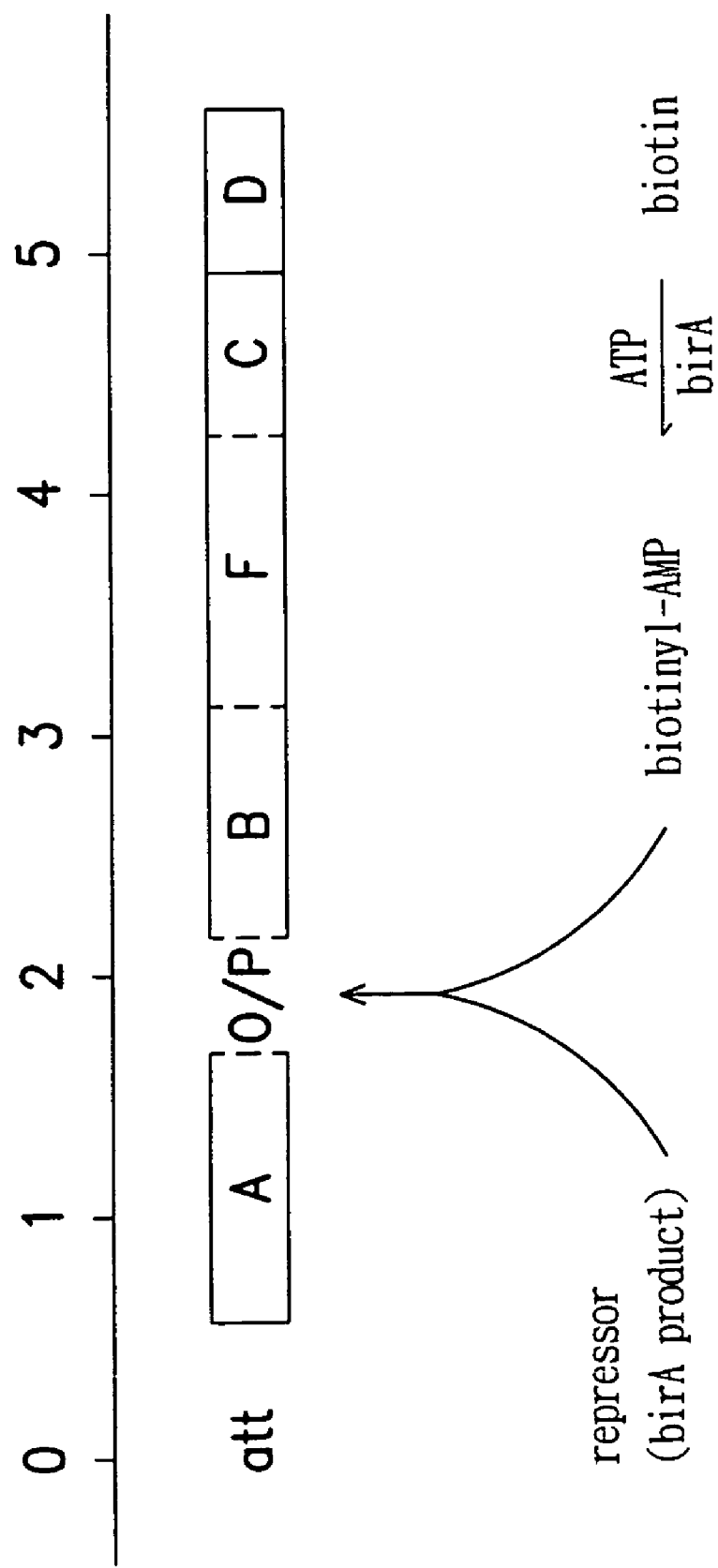
FIG. 1 is a diagram showing the structure and regulation of the biotin operon in E. coli.

The integrated plasmids prepared according to the present invention (see, for example, pMCC21, pMCC31S, pMCC32H, pMCC33U, pMCC35U, pMCC36H, or pMCC38S in FIGS. 6 and 8–13) comprise at least a biotin synthase gene, an assistant DNA sequence for the integration of said plasmid into a host genome, a promoter sequence, and a selection marker. In these plasmids, the BIO2 synthase gene selected from S. cerevisae or C. utilis can express biotin synthase, in the latter of which the nucleotide sequence is set forth in SEQ ID NO:1. The function of biotin synthase is to catalyze the last step of the biotin biosynthesis. This BIO2 gene is cloned and sequenced in the present invention, and the method thereof is described in Example 2 as follows.

The integrated plasmid of the present invention comprises an assistant DNA sequence that assists in the integration of the plasmid into a host genome for recombination. The sequence can be, for example, an 18s ribosomal DNA (rDNA) sequence, which is selected from the 1.7 kb NsiI-BamHI fragment of C. utilis 18s rDNA. In other embodiments, the 18s rDNA sequence is replaced by URA3 or HIS3 DNA fragments (cloned from C. utilis genome), which is effective in the integration of the inventive plasmid into a host genomic DNA.

In the integrated plasmid of the present invention, the promoter sequence is selected from S. cerevisae alcohol dehydrogenase promoter (pADH1) or C. utilis L41 gene promoter (pL41), wherein the pL41 promoter is one of a few number of promoters known in C. utilis.

The selection marker used in the integrated plasmid of the present invention includes, but is not limited to, the mutated L41 gene, which can express the protein having the property of cycloheximide (CHY)-resistance. Therefore, the recombinant colonies can be screened and selected by the presence of cycloheximide when the yeast is cultured (Kondo, K., et al., J. Bacteriol. 177:7171–7177 (1995)).

Those skilled in the art of genetic engineering will be aware that the assistant DNA sequence, promoter sequence, and selection marker described above can be substituted with other analogous sequences without affecting the expression of the desired biotin synthase. Thus, the examples set forth above are only illustrative, but do not limit the scope of the invention.

Another aspect of the present invention provides a method for preparing a yeast with high biotin-productivity, which comprises constructing an integrated plasmid set forth above; linearizing the integrated plasmid, for example, by a restriction enzyme; transforming the linearized integrated plasmid into a yeast, for example, by electroporation; and recombining the biotin synthase gene with the yeast genome. The methods of linearization and transformation are well known to those skilled in the art of genetic engineering and molecular biology.

In addition, the present invention comprises a method of culturing the transformed yeast set forth above in a nutrient medium for a sufficient time, so that biotin can be largely produced. The method further comprises separating, and drying the obtained biotin from the culture broth. Because biotin is a traditional food and feed, the biotin produced by the present invention can be further purified or not, and directly used as, for example, feed additives, food additives, or cosmetics.

The integrated plasmids prepared by the present invention were deposited with the Culture Collection and Research Center, Food Industry Research and Development Institute (Hsinchu, Taiwan), on Jun. 20, 2000, and assigned Accession Number: CCRC 940296 (pMCC21), CCRC 940297 (pMCC31S), CCRC 940298 (pMCC32H), CCRC 940299 (pMCC33U), CCRC 940300 (pMCC35U), CCRC 940301 (pMCC36H), and CCRC 940302 (pMCC38S), respectively.

Without intending to limit it in any manner, the present invention will be further illustrated by the following examples.

EXAMPLE

Example 1

Cloning of *S. cerevisae* BIO2 Gene

The primers containing S all site for cloning were designed according to the BIO2 gene sequence of the *S. cerevisae* Y266 strain as follows as SEQ ID NO: 2 and SEQ ID NO: 3, respectively:

```
Forward: 5'-GAAAGTCGACTCAAGATCTGTCGTACTTAA-3'; and
Reverse: 5'CCGCAGTTAAATCG'ACAACTG'-3'.
```

The DNA fragments of the BIO2 gene were amplified by polymerase chain reaction (PCR).

Example 2

Cloning and Sequencing of *C. utilis* BIO2 Gene

Two conservative amino acid sequence regions were obtained when compared to the biotin synthase gene of five microorganisms belonging to *S. cerevisae, E. coli,* and *Erwinia herbicola*. The degenerate primers were designed according to these conservative regions as follows as SEQ ID NO: 4 and SEQ ID NO: 5, respectively:

```
Forward:  5'-TGTNCNGARGAYTGYAANTATTG-3';
Reverse:  5'-GTRTCNANRTTRTG'GTTGTA-3',
``` wherein Y=T+C, and R=A+G'. About 0.3 kb of DNA fragment was obtained from *C. utilis* genome by PCR. This DNA fragment was used as a probe for screening the complementary sequences from *C. utilis* genomic library prepared by the inventor (using lambda EMBL3 as a vector).

The cloned *C. utilis* biotin synthase gene (GenBank Accession Number AF212161) was sequenced and the nucleotide sequence thereof was as follows (SEQ ID NO: 1):

```
atgtcgtttatattgactgctattagtcgtccgattgctctttccacttc
tagagtagcttctagggctactctggcaacaggtgctactgctgctgcgg
agatcttggaagatgtgttcacggaacaaatggaagaagtggcttcacag
gagaagaagccaaacccattggaatatgcattgtcagtgaagacaccagt
caacacctggaccaaagaagaaattaaagctatatatgacacaccactca
tggacttgatgcactatgctcaggtgcaacacagaaggttccaacaacct
tcagaggttcaattgtgcactcttatgaatatcaaaactggtggttgtac
cgaggactgtaagtactgtgcccaatcacagcgttacaacactggtgtca
aggctgaaagaatcatccaagttgatgaggtgattgaagctgcaaaggag
gcaaaggccaatggatctacaaggttctgtatgggtgctgcttggagaga
gatgaaaggtagaaagtcaaacttgaagaaaatcaaagagatgatcactg
ctgtccatgaccttggaatggagagttgtgtcaccctgggaatggttgat
aaagaccaagccactgaattgaaaagtgctgggttgacggcgtacaacca
taacattgatacttacaaggaacactatccaaaggtgatctccacaagaa
gctttgatgatagattgaaaacattcaaaaacgttcaaggatctggatta
aaggcatgcacaggtggtattcttggtcttggtgagacccaagaggaccg
tgtatctttcctctacaccttggccacaatggatcagcatccagagtctc
ttccaatcaacagactggtcccaatcaagggcacgccaatgtatgaagaa
gttaagaacaagcaagttgaagttgatgagattgtcagaaccattgctac
tgcaagattggtcatgccaacgtctattatcagattggctgcaggaagat
atacaatgaaagaggcagaacaggtgatgtgcttcatggctggttgtaat
gccatcttcacaggtaagaaaatgctcacaacaatgtgtaacggctggga
tgaggataaagccatgttggctaaatggggtctgaaaccaatggagagtt
tcaaatacaaaccaagggaggttgcattcggtgcttga
```

Example 3

Insertion of *C. utilis* BIO2 Gene into *E. coli* Expression Vector pQE30

Figure 7:
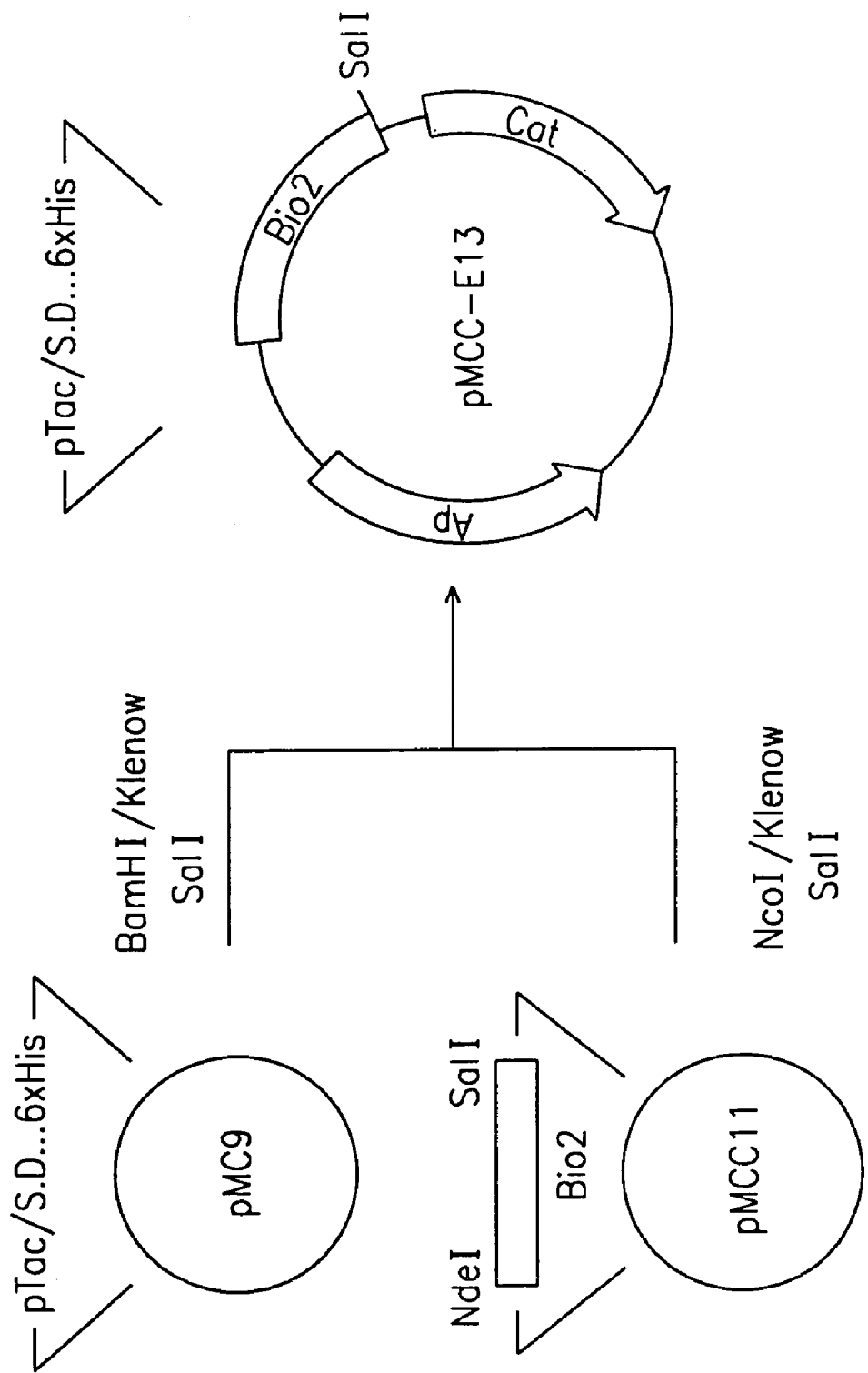
FIG. 7 is a flow chart showing the construct of the pMCC-E13, wherein the plasmid comprises E. coli pTac promoter; and C. utilis biotin synthase BIO2 gene.
Figure 8:
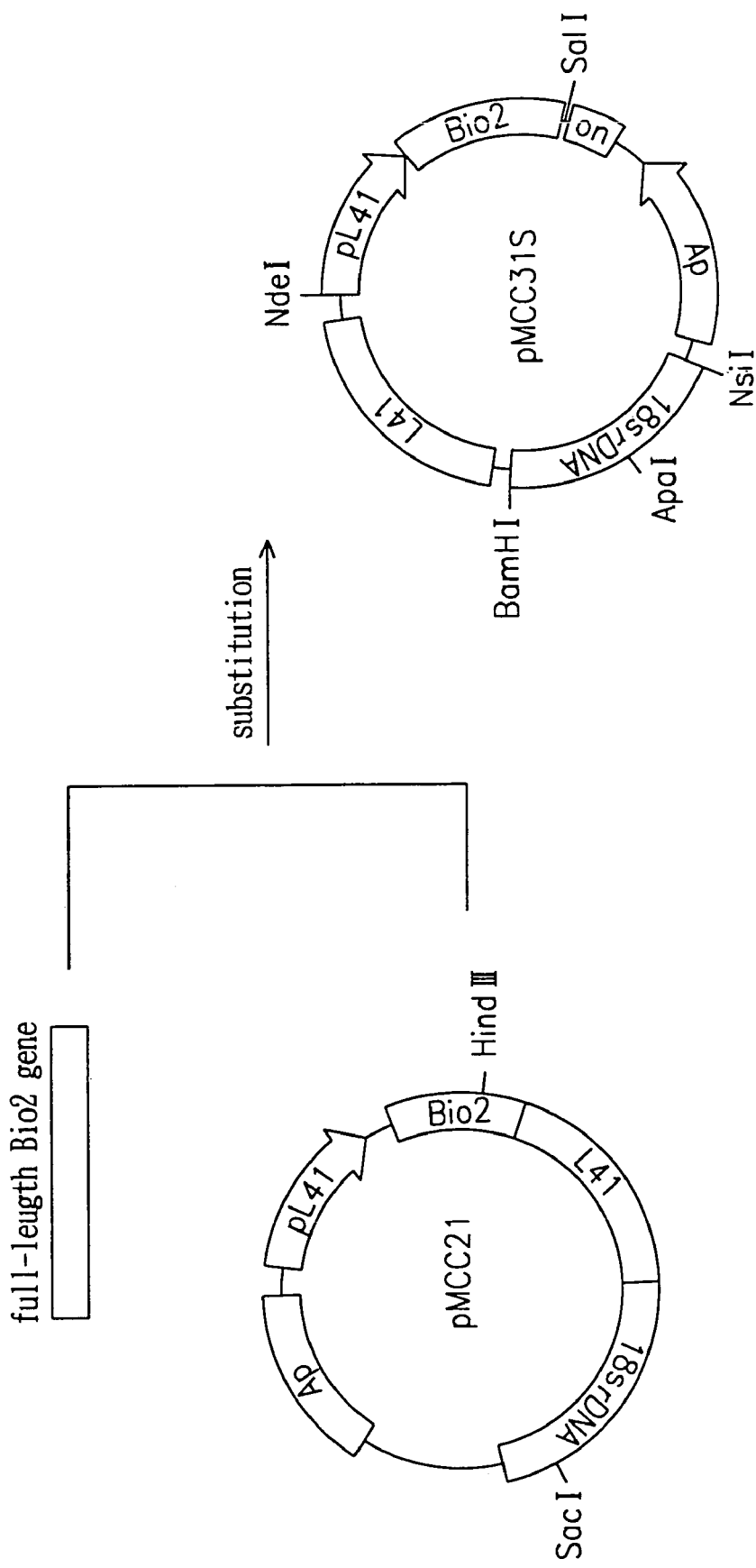
FIG. 8 is a flow chart showing the construct of the pMCC31S, wherein the plasmid comprises C. utilis pL41 for the expression of C. utilis BIO2 gene (encoding for 233 amino acids); mutated L41 gene used as cycloheximide-resistant marker; and C. utilis 18s rDNA.
Figure 9:
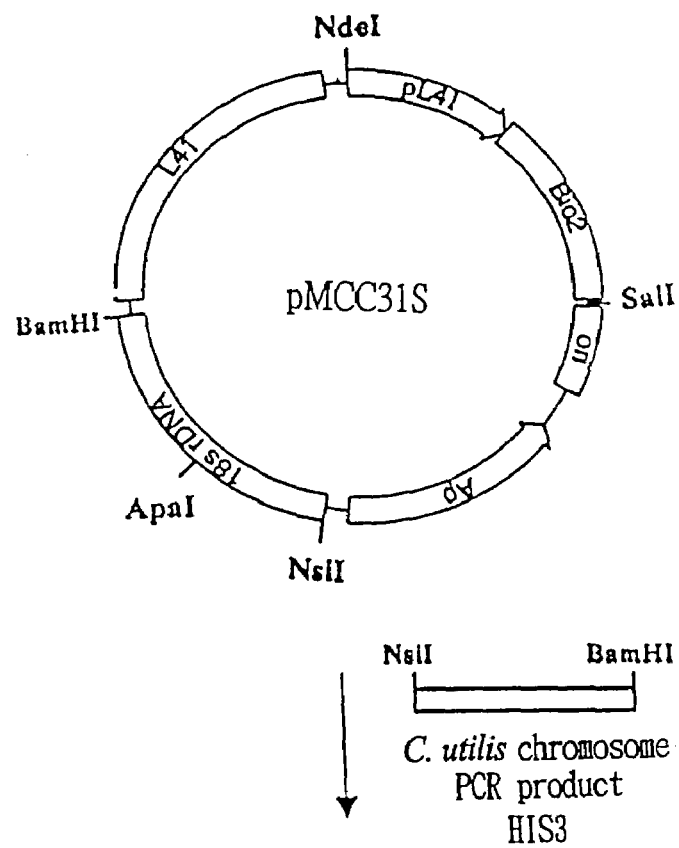
FIG. 9 is a flow chart showing the construct of the pMCC32H, wherein the plasmid comprises C. utilis pL41; C. utilis BIO2 gene; mutated L41 gene used as cycloheximide-resistant marker; and C. utilis HIS3 gene fragment (0.5 kb).
Figure 9:
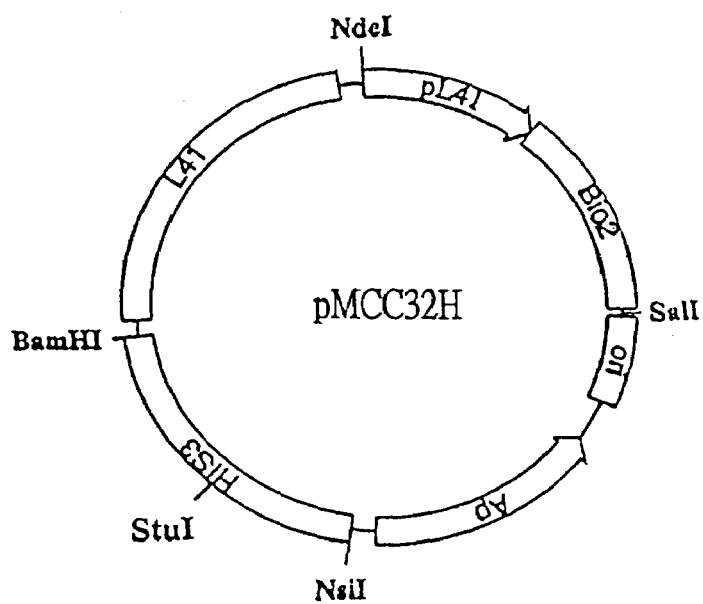
Figure 10:
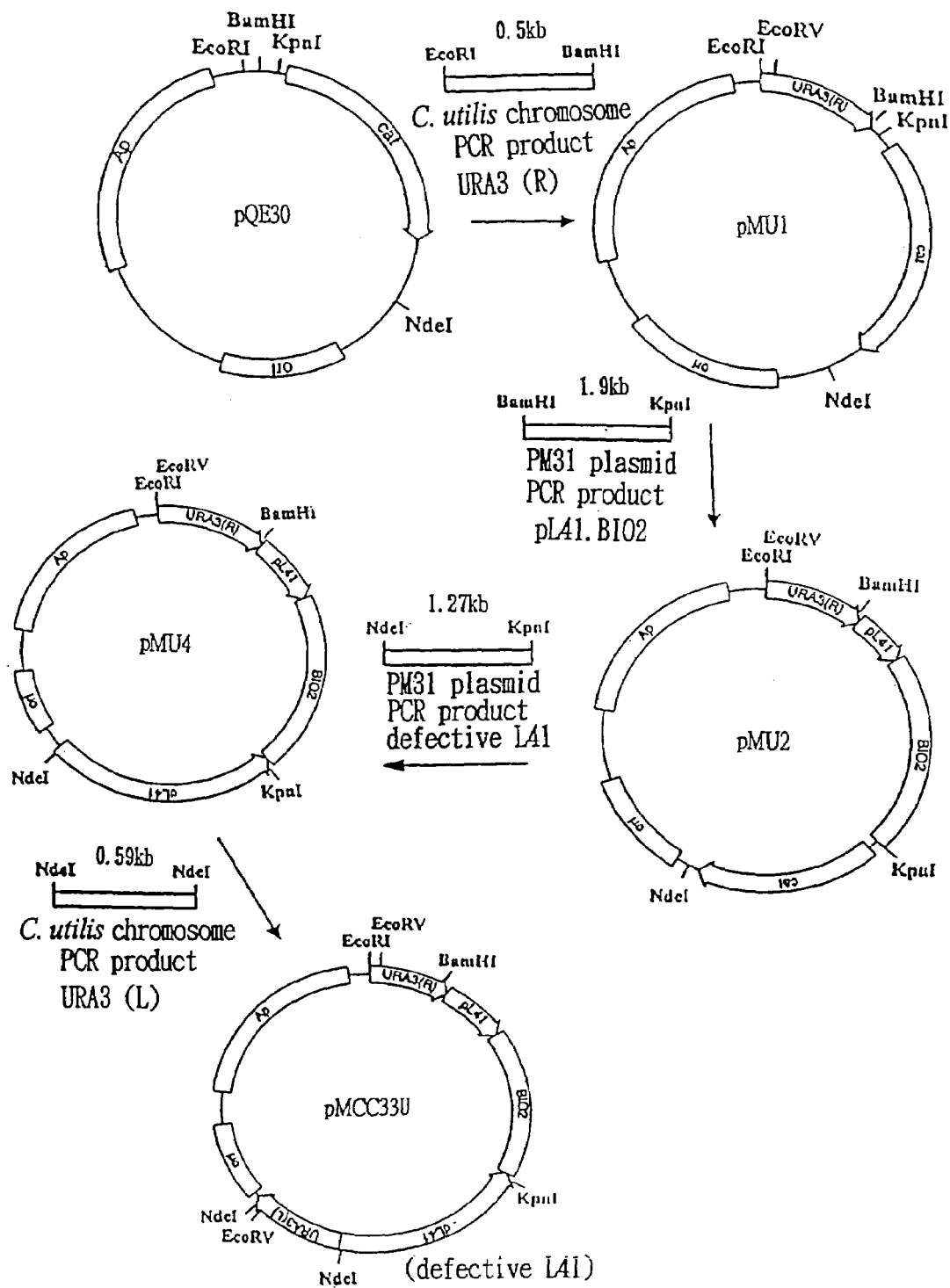
FIG. 10 is a flow chart showing the construct of the pMCC33U, wherein the plasmid comprises C. utilis pL41; C. utilis BIO2 gene; mutated L41 gene used as cycloheximide-resistant marker; and C. utilis URA3 gene fragment (0.59 and 0.50 kb).
Figure 11:
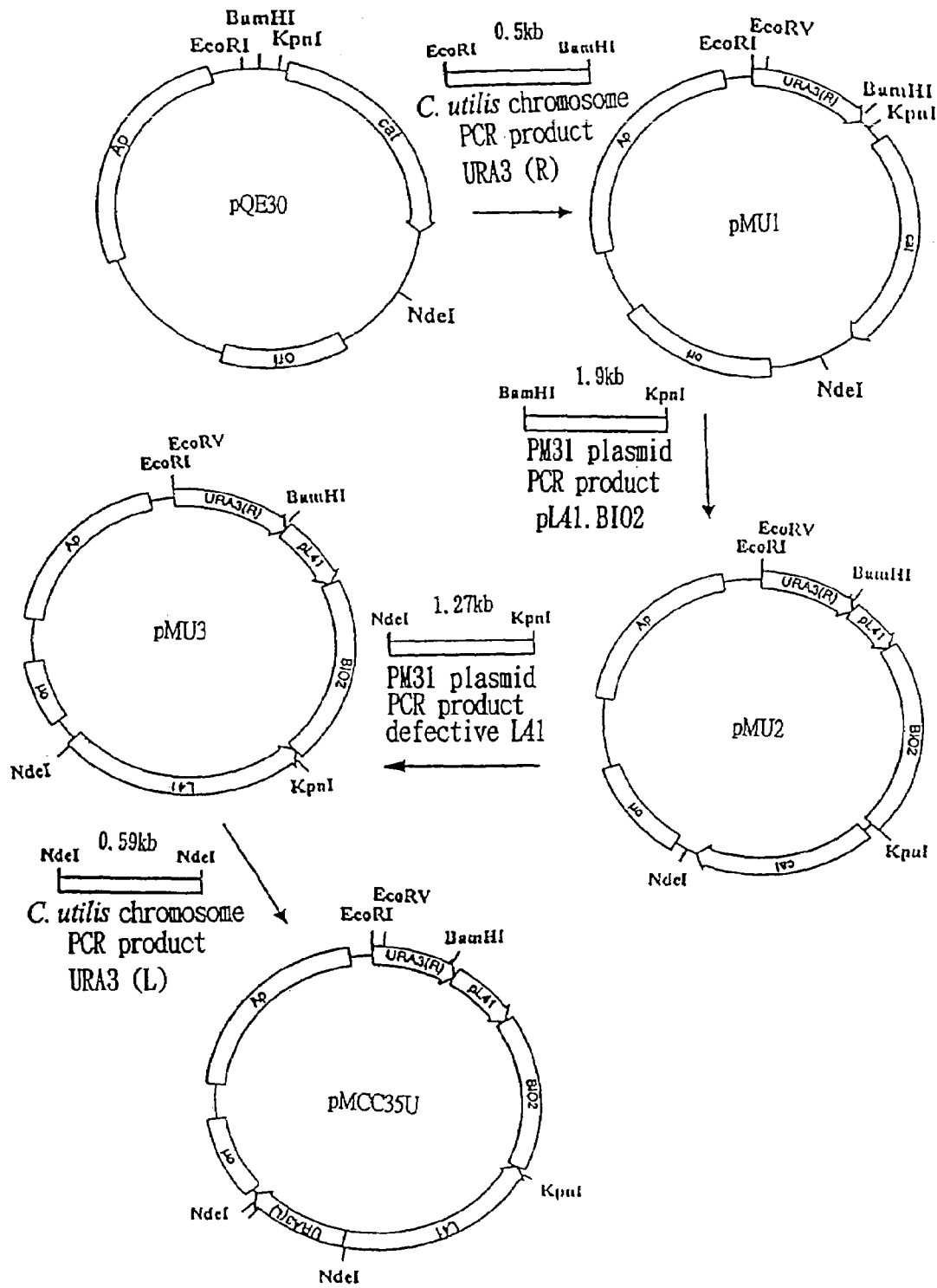
FIG. 11 is a flow chart showing the construct of the pMCC35U, wherein the plasmid comprises C. utilis pL41; C. utilis BIO2 gene; mutated L41 gene used as a cycloheximide-resistant marker; and C. utilis URA3 gene fragment (0.59 and 0.50 kb).
Figure 12:
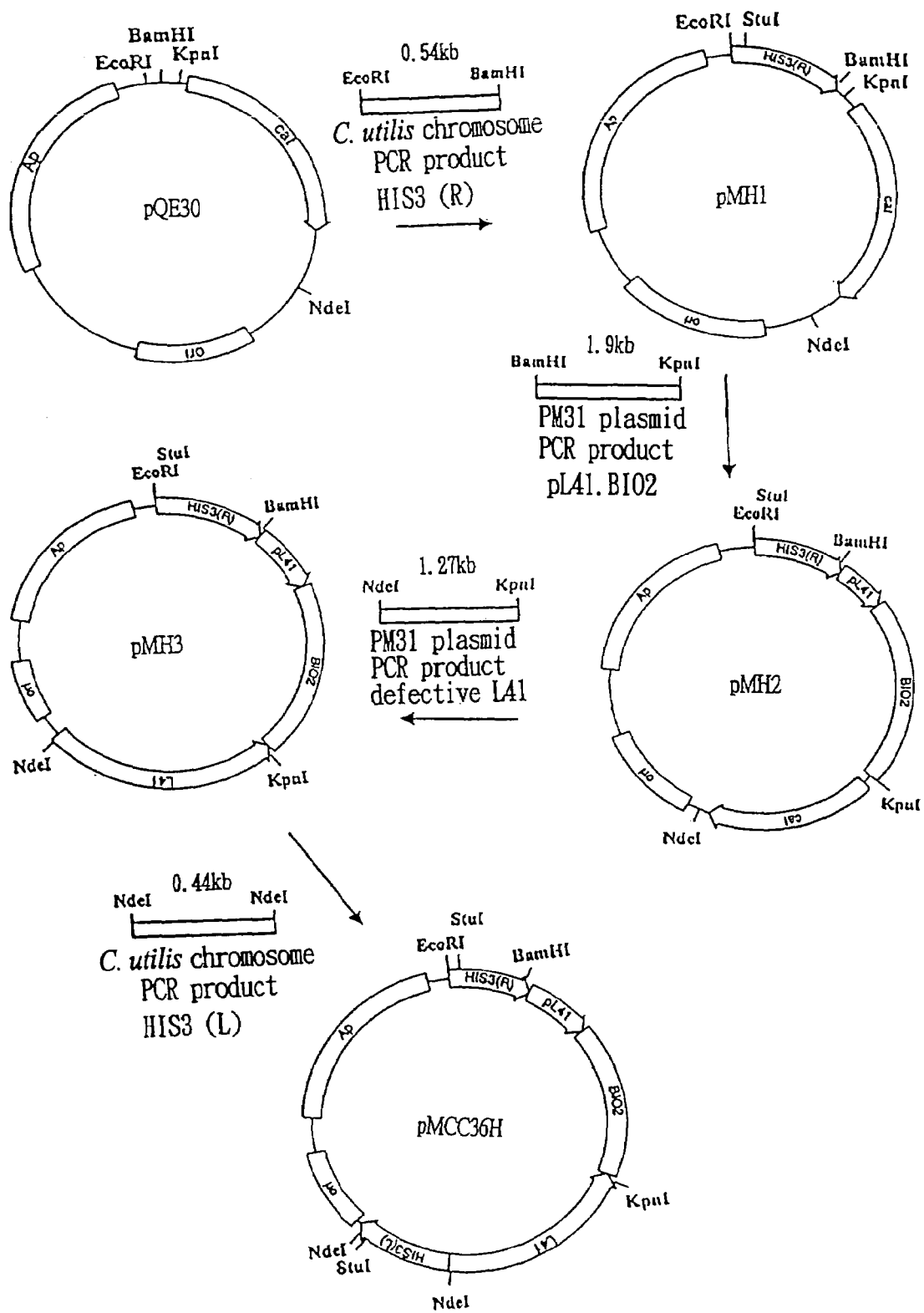
FIG. 12 is a flow chart showing the construct of the pMCC36H, wherein the plasmid comprises C. utilis pL41; C. utilis BIO2 gene; mutated L41 gene used as cycloheximide-resistant marker; and C. utilis HIS3 gene fragment (0.54 and 0.44 kb).
Figure 13:
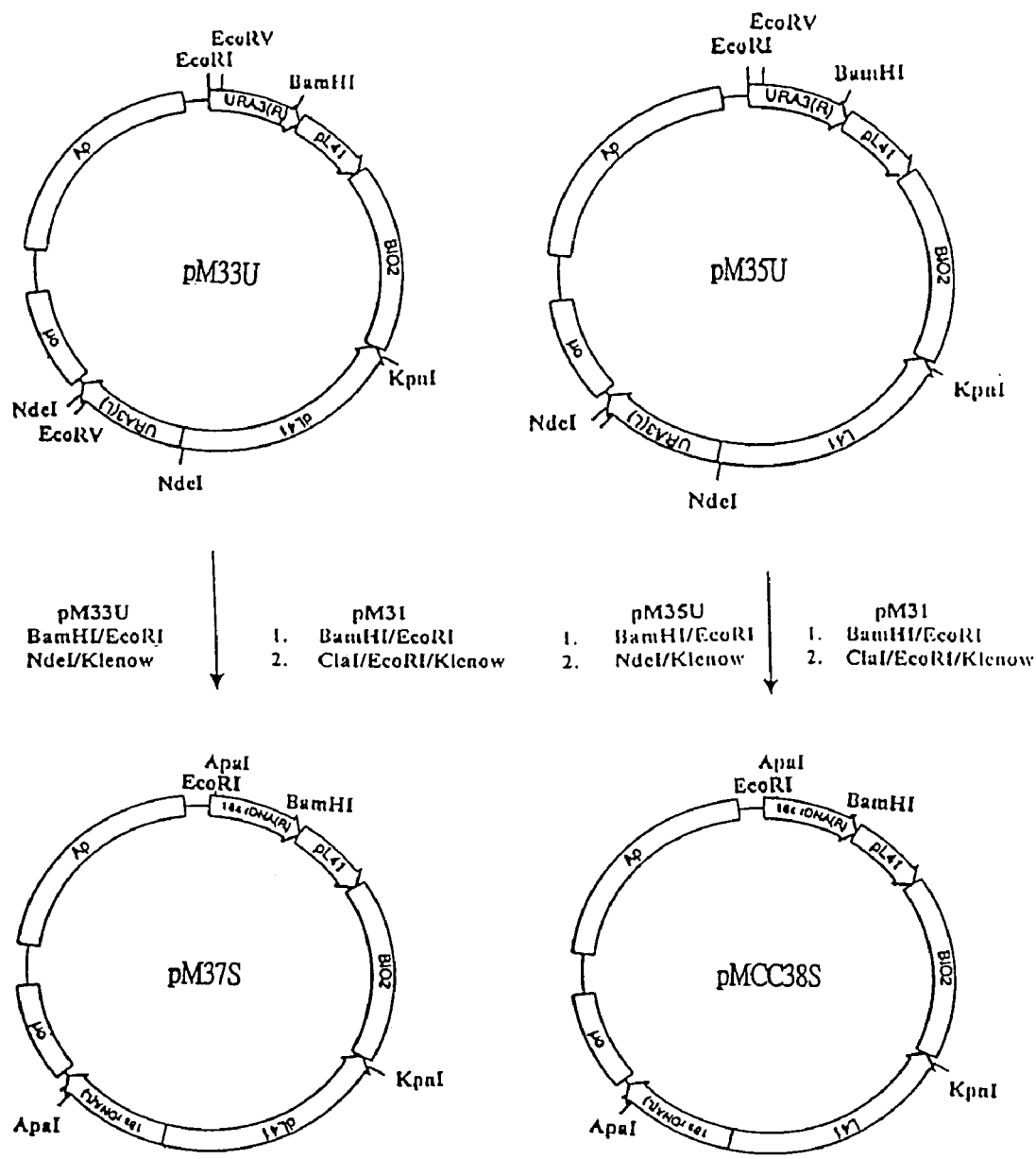
FIG. 13 is a flow chart showing the construct of the pMCC38S, wherein the plasmid comprises C. utilis pL41; C. utilis BIO2 gene; mutated L41 gene used as cycloheximide-resistant marker; and C. utilis 18s rDNA (0.54 and 1.75 kb).

The plasmid pMCC11 and vector pQE30 were digested with NcoI and BamHI, respectively. After digestion, both pMCC11 and vector were end-repaired into blunt ends by Klenow DNA polymerase, followed by SalI digestion. The NcoI/Klenow-SalI fragment of pMCC11 (i.e. BIO2 gene) was integrated into the BamHI/Klenow-SalI site in pQE30 to obtain plasmid pMCC-E13 (FIG. 7). The *C. utilis* BIO2 gene was then expressed in the manner of in-frame fusion by *E. coli* pTac promoter.

Example 4

Activity of C. utilis Biotin Synthase in E. coli

In the E. coli expression system, C. utilis BIO2 gene was induced by IPTG to express biotin synthase, which was then identified by the electrophoresis with SDS-PAGE. The activity of the biotin synthase encoded by the BIO2 gene was measured by lytic complementation as described in Zhang, S., et al., Arch. Biochem. Biophys. 309:29–35 (1994); Hwang, S. Y., et al., J. Biochem. Biophys. Methods 39:111–114 (1999). The plasmid pMCC-E13 was transformed into E. coli DH5α and E. coli R901 (Δbio; with bio operon deleted) strains, respectively. After induction by IPTG, the protein expressed by E. coli DH5α (pMCC-E13) was identified by SDS-PAGE, which was consistent with the putative molecular weight. The complementary experiment was performed by culturing E. coli R901 (pMCC-E13) in the minimal plate supplemented with dithiobiotin (DTB; 50 μg/ml). The result showed that E. coli R901 (pMCC-E13) grew on the plate whereas the E. coli R901 (control) did not. It suggested that C. utilis BIO2 gene obtained from Example 2 was correct due to the enzyme activity (regardless of protein with incomplete 352 amino acids or complete 395 amino acids).

Example 5

Insertion of S. cerevisae BIO2 Gene into Integrated Plasmid

Figure 2:
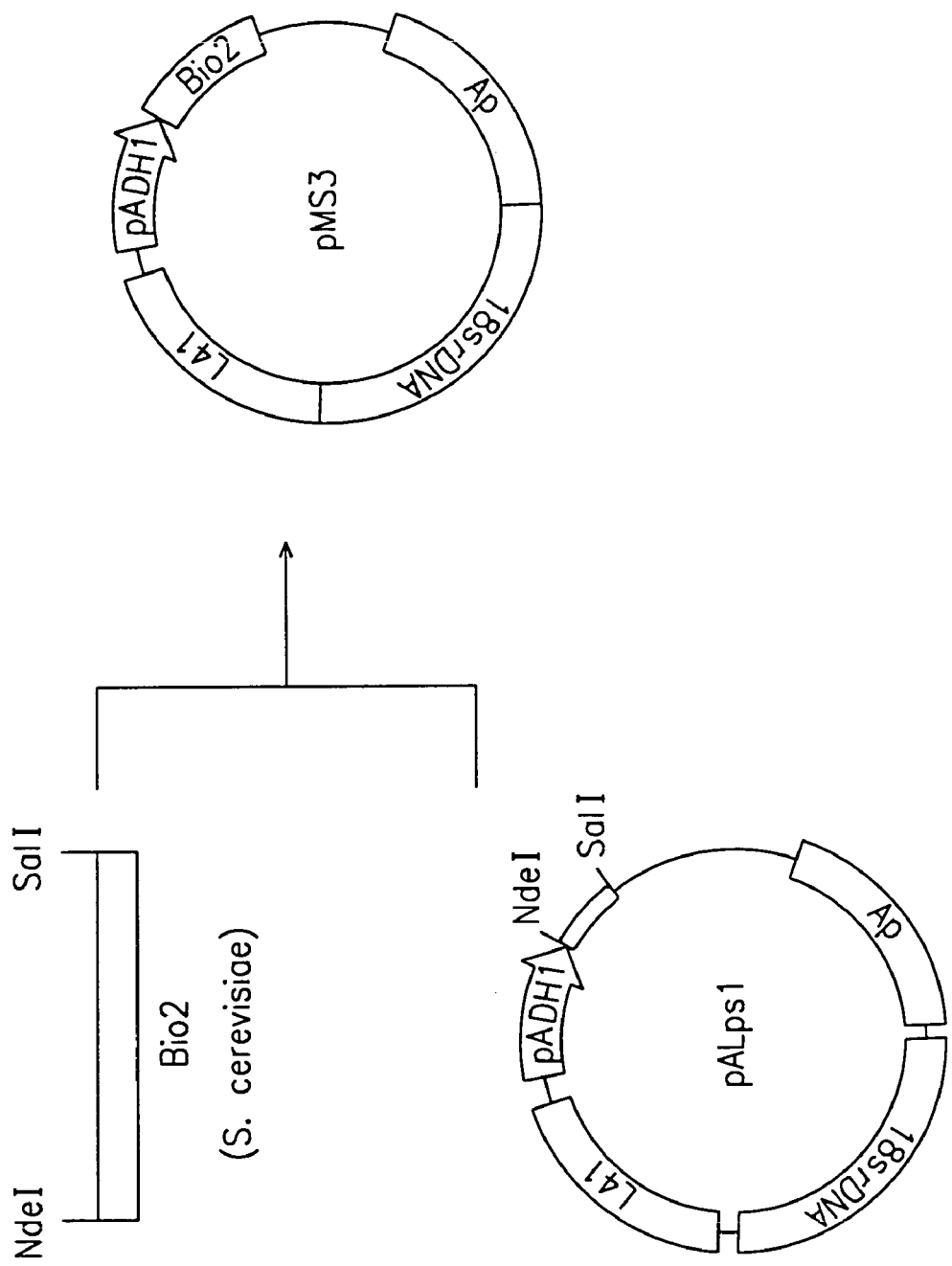
FIG. 2 is a flow chart showing the construct of the pMS3, wherein the plasmid comprises S. cerevisae alcohol dehydrogenase promoter (pADH1) for the expression of BIO2 gene; mutated L41 gene used as cycloheximide-resistant marker; and C. utilis 18s rDNA used for integration.

The PCR products of S. cerevisae BIO2 gene obtained above and vector pALps1 were digested with NdeI-SalI. The digested BIO2 gene was ligated to the treated vector pALps1 at 16° C. for 16 hours to obtain pMS3 (FIG. 2). The plasmid pMS3 herein was comprised of S. cerevisae alcohol dehydrogenase promoter (pADH1) for the expression of BIO2 gene; mutated L41 gene used as cycloheximide-resistant marker; and C. utilis 18s rDNA used for integration.

Figure 3:
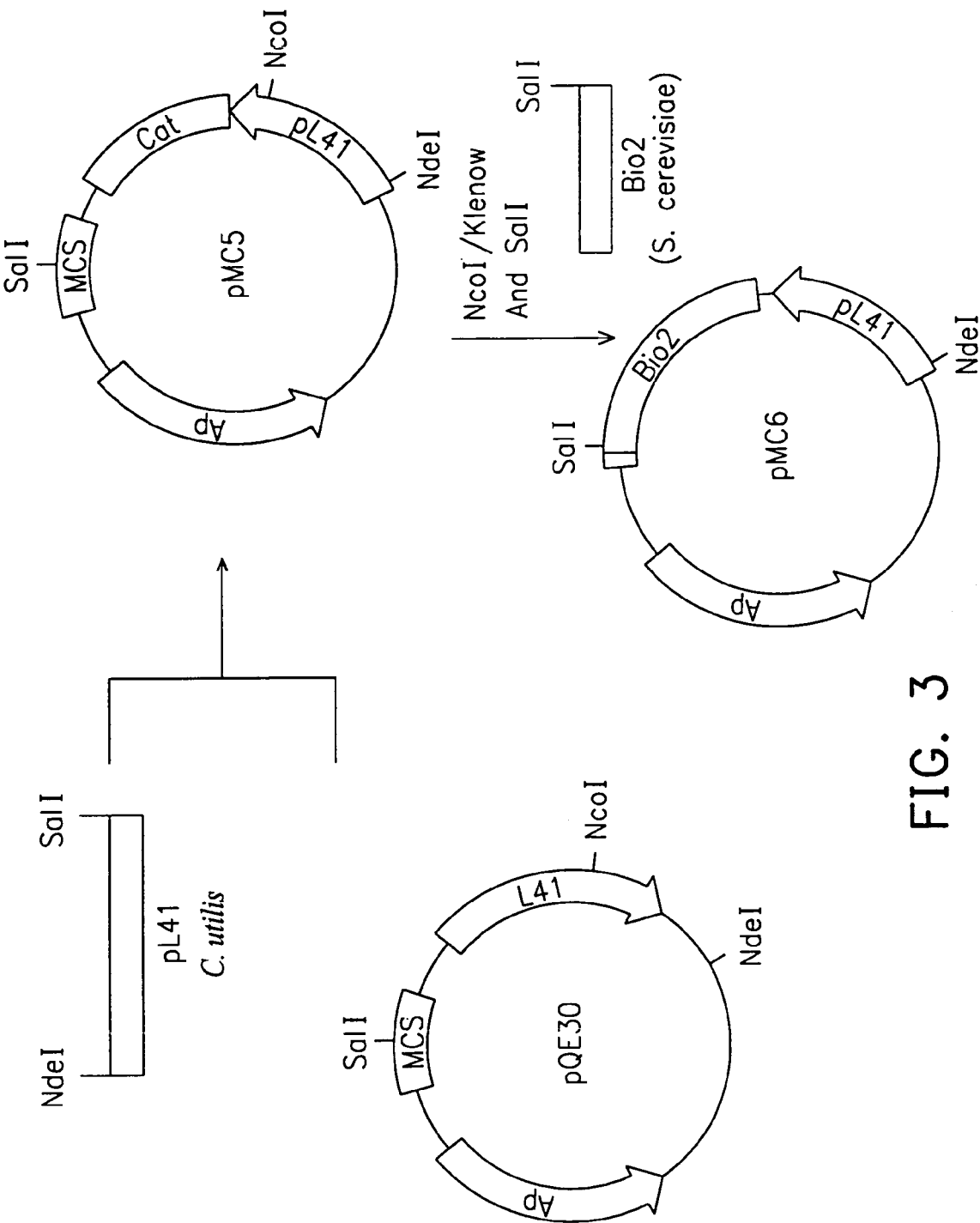
FIG. 3 is a flow chart showing the construct of the pMC6, wherein the plasmid comprises C. utilis L41 gene promoter (pL41); and S. cerevisae biotin synthase gene (BIO2).

Another PCR product of C. utilis L41 promoter (pL41) was digested with NdeI and NcoI, and ligated to pQE30 which was also digested with the same enzymes at 16° C. for 16 hours to obtain pMC5. After digestion with NcoI, plasmid pMC5 was end-repaired into blunt end by Klenow DNA polymerase, and the BIO2 gene was integrated into the NcoI-SalI site of pMC5 to obtain pMC6 (FIG. 3). The plasmid pMC6 herein was comprised of C. utilis L41 gene promoter (pL41) for the expression of S. cerevisae biotin synthase gene.

Figure 4:
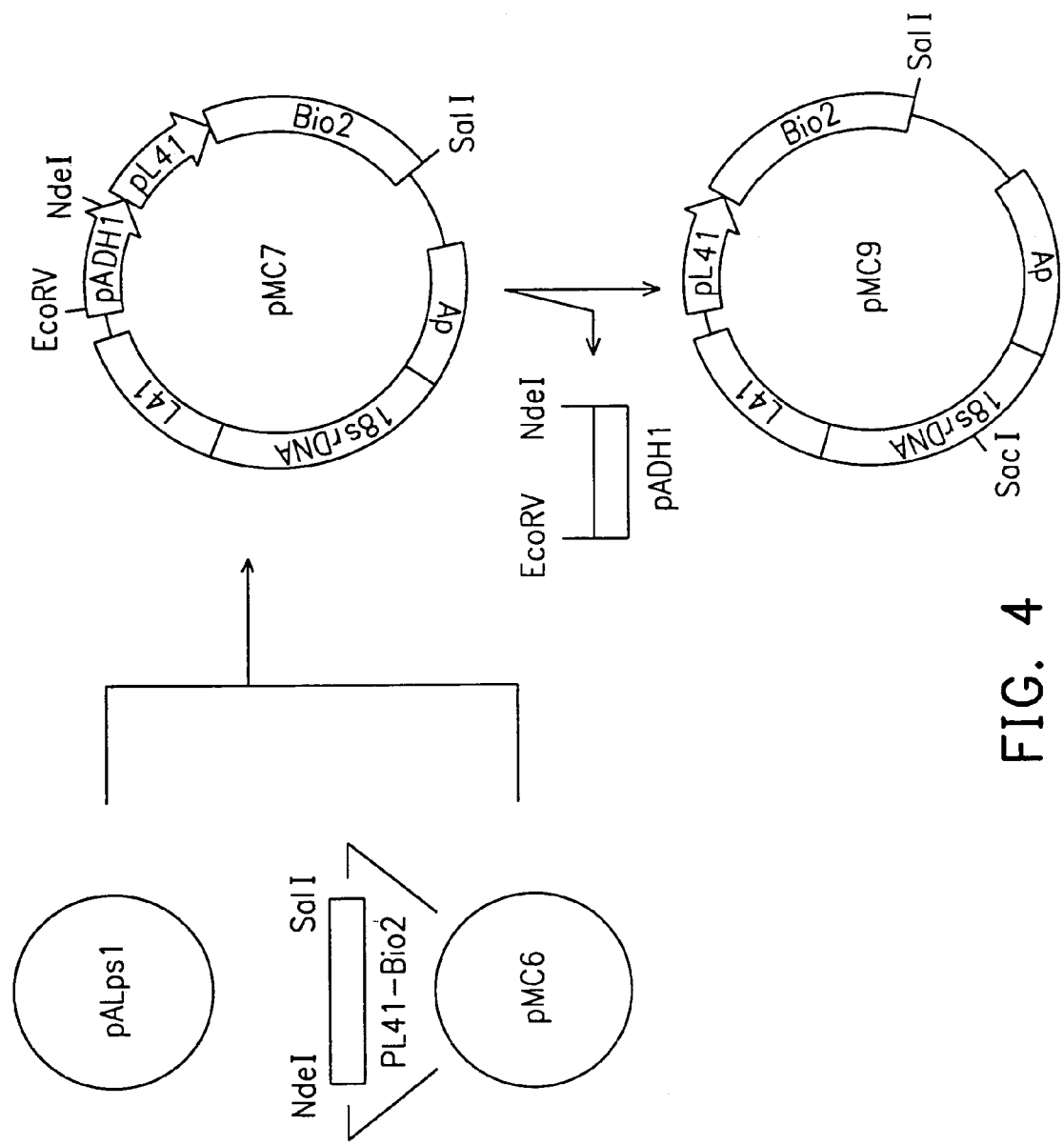
FIG. 4 is a flow chart showing the construct of the pMC9, wherein the plasmid comprises pL41 for the expression of BIO2 gene; mutated L41 gene used as cycloheximide-resistant marker; and C. utilis 18s rDNA.

The NcoI-SalI fragment of pMC6 (i.e. pL41-BIO2) was ligated to vector pALps1 under the same conditions to obtain pMC7. After removal of EcoRV-NdeI fragment of pMC7 (i.e. S. cerevisae pADH1 promoter sequence), the plasmid pMC9 was obtained (FIG. 4). The plasmid pMS3 and pMC9 used S. cerevisae pADH1 and C. utilis pL41 promoters, respectively, to regulate S. cerevisae BIO2 gene. In addition, both plasmids were integrated plasmids capable of integration into C. utilis.

Example 6

Insertion of C. utilis BIO2 Gene into Integrated Plasmid

Figure 5:
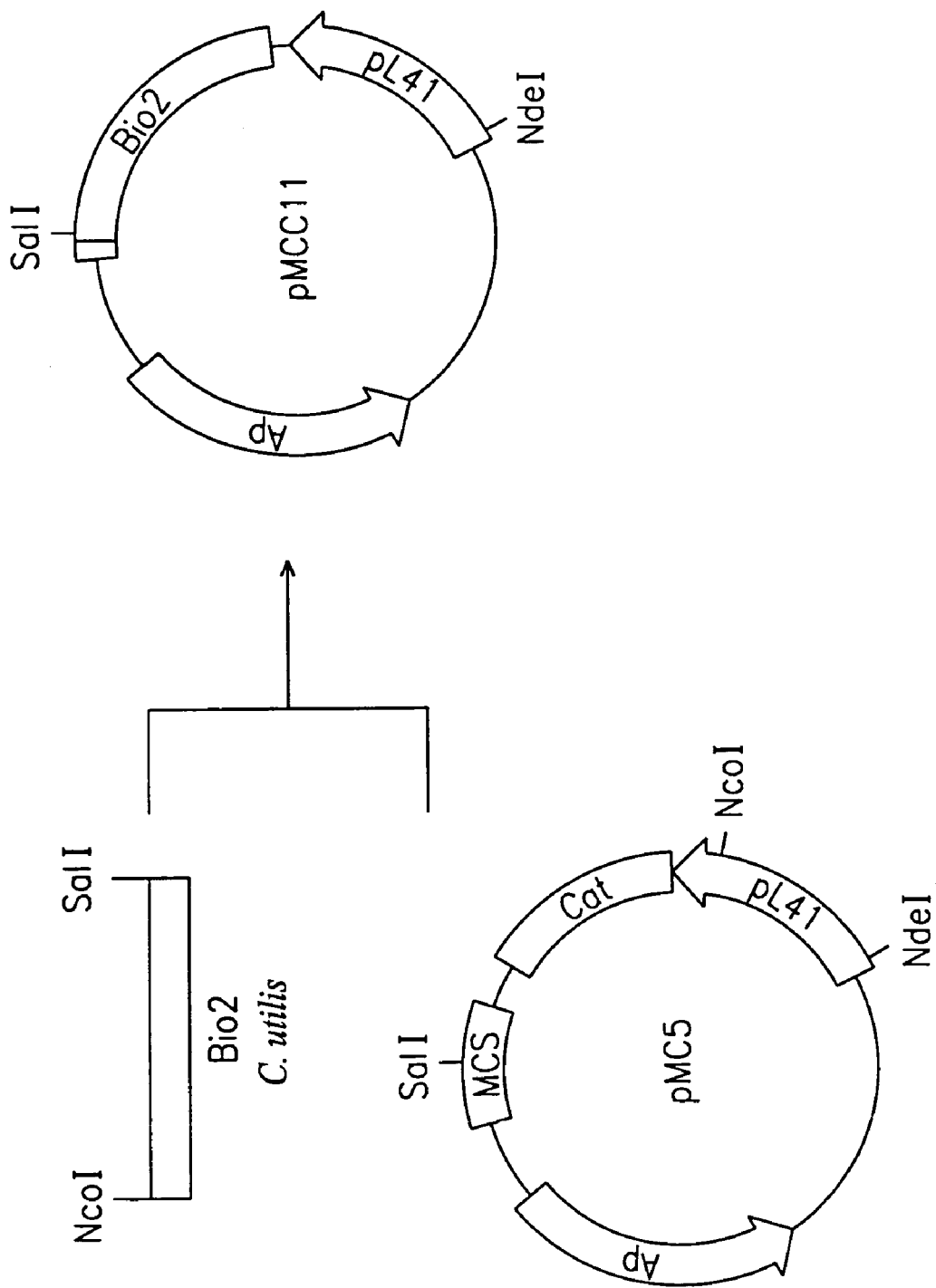
FIG. 5 is a flow chart showing the construct of the pMCC11, wherein the plasmid comprises C. utilis L41 gene promoter (pL41); and C. utilis biotin synthase BIO2 gene.
Figure 6:
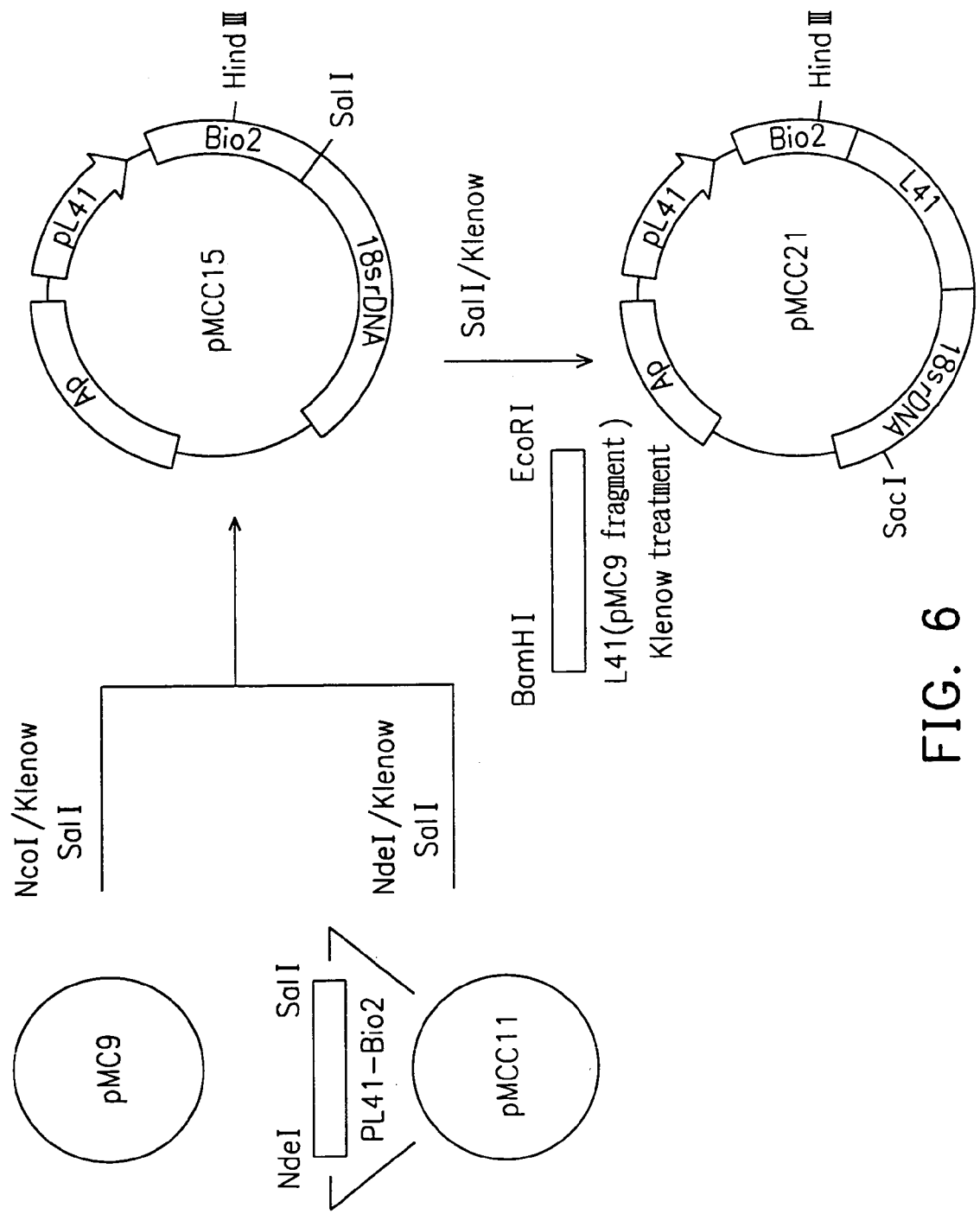
FIG. 6 is a flow chart showing the construct of the pMCC21, wherein the plasmid comprises pL41 for the expression of C. utilis BIO2 gene (encoding for 204 amino acids); mutated L41 gene used as cycloheximide-resistant marker; and C. utilis 18s rDNA.

By the primers designed for suitable cleavage sites, the PCR was carried out using the C. utilis BIO2 gene obtained from Example 2 as a template. The product was digested with NdeI and SalI, and ligated into pMC5 to obtain pMCC11 (FIG. 5). Afterwards, as shown in FIG. 6, the NdeI-SalI fragment of pMCC11 in which the NdeI nickel was end-repaired into a blunt end by Klenow DNA polymerase (i.e. pL41-BIO2 fragment) and was ligated into pMC9 to obtain pMCC15. To fill the lost L41 fragment, the BamHI-EcoRI fragment of pMC9 (i.e. L41 gene fragment) was end-repaired into a blunt end by Klenow DNA polymerase and then integrated into the SalI site in pMCC15 to obtain pMCC21. The plasmid pMCC21 herein was comprised of C. utilis pL41 for the expression of the C. utilis BIO2 gene; mutated L41 gene used as cycloheximide-resistant marker; and C. utilis 18s rDNA.

Example 7

Other Integrated Plasmid Constructs

The preparations of the other integrated plasmids such as pMCC31S, pMCC32H, pMCC33U, pMCC35U, pMCC36H, and pMCC38S were schematically shown in FIGS. 9–13.

Example 8

Transformation of C. utilis and Flask Fermentation Test

The plasmid pMC9 was linearized by NcoI and transformed into C. utilis using electroporation. The obtained transformants were named as m9-101, m9-102, etc., wherein the S. cerevisae BIO2 gene was regulated by pL41 promoter. Another plasmid pMCC21 was linearized by SacI and transformed into C. utilis using electroporation. The obtained transformants were named as m21-101, m21-102, etc., wherein the C. utilis BIO2 gene was regulated by the pL41 promoter.

Those transformants obtained above were cultured in YPD medium (or YPD with 40 μg/ml cycloheximide) for 72 hours. Cells were lysed by French Press (12,000 psi), and then the biotin was quantified using competitive ELISA.

The results are shown in Table 1. Beside 23 ng/ml biotin originally present in YPD medium, only 8.2 ng/ml biotin is produced by the wild type (WT) yeast. However, the biotin productivity is markedly increased in each transformant. The differences among the transformants may be related to the copy number of the integrated plasmid. On average, the biotin content in m9 transformants is 860 ng/ml and that in m21 transformants is 720 ng/ml, which is 103 and 87 times of that of wild type yeast, respectively.

TABLE 1

Analysis of Biotin Content in C. utilis Transformants

| | Culture Broth | | | | Cell Extract | | |
| --- | --- | --- | --- | --- | --- | --- | --- |
| | OD$_{660\,nm}$ | YPD (ng/ml) | OD$_{660\,nm}$ | YPD (CHY) (ng/ml) | YPD (ng/ml) | YPD (CHY) (ng/ml) | incubator |
| YPD | | 23 | | | | | |
| WT | 8.72 | 26 | | | 5.3 | | |
| m9-101 | 9.05 | 860 | 8.04 | 660 | 66 | 63 | Flask (50 ml) |
| m9-102 | 8.75 | 760 | 2.28 | 714 | 86 | 7.3 | Flask (50 ml) |
| m9-103 | 5.12 | 920 | | | | | Tube (3 ml) |
| m9-104 | 8.40 | 1010 | | | | | Tube (3 ml) |
| m9-105 | 8.90 | 900 | | | | | Tube (3 ml) |
| m9-106 | 6.00 | 750 | | | | | Tube (3 ml) |
| m9-107 | 5.96 | 460 | | | | | Tube (3 ml) |
| m21-101 | 8.44 | 600 | 2.56 | 620 | 98 | 6 | Flask (50 ml) |
| m21-102 | 6.28 | 802 | 4.72 | 964 | 111 | 13 | Flask (50 ml) |
| m21-103 | 3.60 | 420 | | | | | Tube (3 ml) |
| m21-104 | 8.54 | 720 | | | | | Tube (3 ml) |
| m21-105 | 838 | 430 | | | | | Tube (3 ml) |
| m21-106 | 4.86 | 560 | | | | | Tube (3 ml) |

Note: m9 strains represent C. utilis O(pMC9, comprising pL41 and S. cerevisae B102 gene); m21 strains represent C. utilis (pMC21, comprising pL41 and C. utilis B102 gene).

From the results shown above, the integrated plasmids of the present invention comprising isolated biotin synthase gene and 18s rDNA or URA3 or HIS3 sequence largely express biotin under a suitable regulation. In addition, the resulting yeast with high biotin-productivity can be directly used as feed additives, food additives, or cosmetics without further purification.

While the invention has been particularly shown and described with the reference to the preferred embodiment thereof, it will be understood by those skilled in the art that various changes in form and details may be made without departing from the spirit and scope of the invention.

What is claimed is:

1. A method for preparing yeast with improved biotin-productivity, comprising the steps of:
   (a) providing an integrating plasmid comprising:
   (i) a promoter sequence that is functional in yeast, and which is operably linked to a polynucleotide sequence encoding *Candida utilis* biotin synthase, wherein the polynucleotide sequence encoding *Candida utilis* biotin synthase comprises the nucleotide sequence of SEQ ID NO: 1;
   (ii) an assistant DNA sequence to promote integration into a host genome; and
   (iii) a polynucleotide sequence encoding a yeast selectable marker;
   (b) linearizing said integrating plasmid; and
   (c) transforming said linearized integrating plasmid into the yeast under conditions that permit recombination between the *Candida utilis* biotin synthase gene and the yeast genome.

2. The method as claimed in claim 1, wherein the assistant DNA sequence is a *Candida utilis* fragment selected from the group consisting of NsiI-BamHI 18s rDNA, URA3 DNA, and HIS3 DNA.

3. The method as claimed in claim 1, wherein the selection marker is a cycloheximide-resistance gene.

4. The method as claimed in claim 1, wherein the promoter sequence is selected from the group consisting of L41 promoter of *Candida utilis* and ADH1 promoter of *Saccharomyces cerevisae*.

5. The method as claimed in claim 1, wherein the prepared yeast with improved biotin-productivity is useful in feed additives, food additives, or cosmetics.

* * * * *